United States Patent [19]

Anderson et al.

[11] Patent Number: 4,472,392

[45] Date of Patent: Sep. 18, 1984

[54] SULFONATE CONTAINING ESTER PRODRUGS OF CORTICOSTEROIDS

[75] Inventors: Bradley D. Anderson, Kalamazoo; Robert A. Conradi, Portage, both of Mich.

[73] Assignee: The Upjohn Company, Kalamazoo, Mich.

[21] Appl. No.: 459,742

[22] Filed: Jan. 21, 1983

[51] Int. Cl.$^3$ ............................................. A61K 31/56
[52] U.S. Cl. ................................ 424/243; 260/397.45
[58] Field of Search ..................... 260/397.45; 424/243

[56] References Cited

U.S. PATENT DOCUMENTS 4,264,585 4/1981 Baungarth et al. ............ 260/397.45
4,296,109 10/1981 Laurent et al. ....................... 424/241

FOREIGN PATENT DOCUMENTS 2325358 11/1973 Fed. Rep. of Germany .
 940701 10/1963 United Kingdom .
1007925 10/1965 United Kingdom ........... 260/397.45
1087730 10/1967 United Kingdom ........... 260/397.45
1180176 2/1970 United Kingdom ........... 260/397.45

OTHER PUBLICATIONS

Anderson, B. D. and Taphouse, V., J. Pharm. Sci. 70 (2), Feb. 1981, pp. 181–186, "Initial Rate Studies of Hydrolysis and Acyl Migration in Methylprednisolone 21-Hemisuccinate and 17-Hemisuccinate".
Flynn, G. L. and Lamb, D. J., J. Pharm. Sci. 59 (10), Oct. 1970, pp. 1433–1438, "Factors Influencing Solvolysis of Corticosteroid-21-phosphate Esters".
Garrett, E. R., J. Pharm. Sci. 51 (5), May 1962, pp. 445–450, "Prediction of Stability in Pharmaceutical Preparations X: Alkaline Hydrolysis of Hydrocortisone Hemisuccinate".
Kawamura, M., et al., Yakugaku Zasshi, 91 (8), 1971, pp. 863–870, "Pharmaceutical Studies on Water-soluble Corticosteroid Derivatives, II. Stability of Hydrocortisone 21-Aminoalkylcarboxylates in Solution".
Kawamura, M., et al., Yakugaku Zasshi, 91 (8), 1971, pp. 871–878, "Pharmaceutical Studies on Water-soluble Corticosteroid Derivatives, III. Stability of Hydrocortisone 21-Sulfobenzoates and 21-Sulfate in Solution".
Yamamoto, R., et al., Yakugaku Zasshi, 91 (8), 1971, pp. 855–862, "Pharmaceutical Studies on Water-soluble Corticosteroid Derivatives, I. Stability of Hydrocortisone 21-Hemiesters in Solution".

*Primary Examiner*—Elbert L. Roberts
*Attorney, Agent, or Firm*—L. Ruth Hattan

[57] ABSTRACT

Novel solution stable ester prodrugs of corticosteroids of the formula

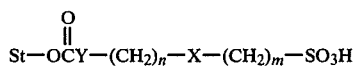

and their salts.

14 Claims, No Drawings

SULFONATE CONTAINING ESTER PRODRUGS OF CORTICOSTEROIDS

BACKGROUND OF THE INVENTION

Conventional anti-inflammatory steroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. The term "prodrug" denotes a derivative of an active drug which is converted after administration back to the active drug. The "pro-moiety" referred to in this application is the fragment attached to the steroid via an ester linkage and removed by ester hydrolysis in vivo. A major problem with many common derivatives is their solution instability. Dicarboxylic acid hemiesters of corticosteroids such as succinate esters, for example, are marketed commercially as lyophilized powders for reconstitution prior to injection due to their solution instability (see, for example, E. R. Garrett, *J. Pharm. Sci.*, 51, 445 (1962); B. D. Anderson and V. Taphouse, *J. Pharm. Sci.*, 70, 181; R. Yamamoto, S. Fujisawa, and M. Kawamura, *Yakugaku Zasshi*, 91, 855 (1971)).

Corticosteroid 21-aminoalkyl carboxylate derivatives reported in the literature also undergo rapid hydrolysis in aqueous solution (M. Kawamura, R. Yamamoto, and S. Fujisawa, *Yakugaku Zasshi*, 91, 863 (1971)).

Certain derivatives which do appear to exhibit better solution stability suffer from other disadvantages. 21-sulfate esters, for example, may not be readily converted to the active parent drug in vivo as suggested by the fact that the 21-sulfate of hydrocortisone is inactive in mice (M. Kawamura, R. Yamamoto, and S. Fujisawa, *Yakugaku Zasshi*, 91, 871 (1971); meta-sulfobenzoate esters which have been reported as having improved solution stability (M. Kawamura, R. Yamamoto and S. Fujisawa, ibid, French Patent Derwent No. 76199 U)) are frequently not highly water soluble and thus may have limited utility as injectable prodrugs. Phosphate esters may in some cases possess the requisite solubility, solution stability, and bioconversion rates but exhibit other disadvantages. Several undesirable features of phosphate esters are apparent: (1) Phosphate esters are often difficult to purify and are frequently very hygroscopic. (2) The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid due to micelle formation by the intact prodrug is a desirable feature which phosphate esters exhibit to only a limited extent. (4) Concentrated solutions of phosphate esters of corticosteroids exhibit accelerated reaction velocities due to micelle formation, limiting shelf-life in concentrated solutions (G. L. Flynn and D. J. Lamb, *J. Pharm. Sci.*, 1433 (1970)). Sulfopropionate esters of corticosteroids have also been reported as readily water soluble and having improved solution stability (Derwent Accession No. 27789C). Sulfoacetate esters are also known (Derwent 9453F). The esters claimed in the present invention are significantly more stable than sulfoacetate or sulfopropionate esters.

FIELD OF INVENTION

The present invention is novel sulfonate containing ester prodrugs of corticosteroids and formulations of steroid prodrugs.

SUMMARY OF INVENTION

The compounds of the present invention are sulfonate containing ester prodrugs of corticosteroids which are solution stable in vitro but are rapidly converted in vivo to the active parent drug and are therefore useful as anti-inflammatory agents. The compounds of the present invention are represented by the following general Formula I and their salts with pharmaceutically acceptable bases:

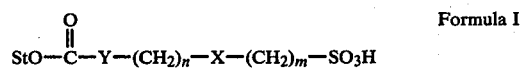

Formula I wherein St represents a corticosteroid moiety bonded to the carbonyl via the 21-hydroxyl group of said corticosteroid; Y is a bond, or —O—, X is

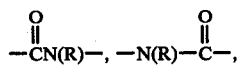

—O—, —S—, —(O)—, or —S(O$_2$)—;

n is an integer of from 2 to 9;

m is an integer of from 1 to 5; with the proviso that the sum of m and n is not greater than 10;

R is H or lower alkyl of from 1 to 4 carbon atoms with the proviso that when n is 2, R is other than hydrogen;

Pharmaceutically acceptable base addition salts of the compounds of Formula I are also a part of the present invention. Any reference herein to the compounds of Formula I is intended to include pharmaceutically acceptable salts thereof. Solution stable formulations of the compounds of Formula I are also a part of the present invention.

DETAILED DESCRIPTION OF INVENTION

In the compounds of general Formula I St represents the parent corticosteroid minus the 21-hydroxyl group of said corticosteroid which is necessary to form the novel esters of the present invention. The parent corticosteroid could be depicted as StOH wherein the OH is located at the 21-position of the corticosteroid which may be depicted as follows:

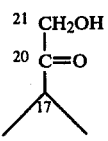

Of course the carbon atoms at positions C-17 and C-21 may be substituted as will be apparent from the description hereinbelow.

The term corticosteroid as used herein it taken to mean not only the steroids produced by the adrenal cortex but also synthetic equivalents, i.e., non-naturally occurring steroids which possess physiological properties characteristic of naturally occurring corticosteroids. Reference is made to *Drill's Pharmacology in Medicine*, McGraw-Hill Book Company, New York, (1965), Chapter 73: Adrenal Cortex and Adrenocortical Hormones, particularly pages 1185–1187 wherein typical corticosteroids employed in the present invention are described. Also, typical corticosteroids represented by StOH include those described in Applezweig, *Steroid Drugs,* McGraw-Hill Book Company, Inc., New York, 1962, pp. 435–731, and in particular the compounds associated with the following parenthetical numbers:

675; 684; 685; 734; 1030; 1033; 1034; 1035; 1036; 1038; 1039; 1048; 1051; 1052; 1059; 1061; 1063; 1064; 1066; 1067; 1068; 1070; 1071; 1072; 1073; 1078; 1080; 1082; 1083; 1084; 1086; 1087; 1088; 1092; 1093; 1094; 1095; 1099; 1100; 1101; 1105; 1107; 1108; 1109; 1110; 1111; 1112; 1116; 1116-A; 1117; 1119; 1120; 1121; 1125; 1128; 1135; 1140; 1141; 1142; 1143; 1149; 1151; 1155; 1168; 1169; 1170; 1172; 1173; 1174; 1175; 1176; 1178; 1181; 1182; 1182-A; 1183; 1184; 1186; 1187; 1189; 1193; 1194; 1197; 1198; 1206; 1207; 1214; 1215; 1216; 1217; 1218; 1220; 1221; 1226; 1227; 1230; 1231; 1242; 1243; 1244; 1246; 1248; 1251; 1270; 1272; 1273; 1274; 1275; 1279; 1280; 1281; 1282; 1283; 1285; 1286; 1287; 1294; 1295; 1296; 1306; 1307; 1308; 1319; 1320; 1322; 1323; 1324; 1325; 1327; 1328; 1329; 1330; 1331; 1333; 1334; 1336; 1337; 1338; 1339; 1340; 1350; 1351; 1352; 1363; 1368; 1370; 1385.

Also, typical corticosteroids represented by StOH include those described in Applezweig, *Steroid Drugs,* Holden-Day, Inc., San Francisco, 1964, pp. 109–438, and in particular the compounds associated with the following "catalogue" numbers:

2680; 2681; 2709; 2713; 2714; 2716; 2717; 2719; 2720; 2722; 2723; 2724; 2725; 2726; 2727; 2728; 2729; 2730; 2731; 2732; 2733; 2734; 2735; 2736; 2737; 2738; 2739; 2740; 2741; 2742; 2743; 2744; 2745; 2746; 2814; 2826; 2827; 3036-A; 3036-B; 3036-C; 3036-D; 3036-E; 3036F; 3036-G; 3036-H; 3036-I; 3036-J; 3036-K; 3036-L; 3036-M; 3036-N; 3036-O; 3036-P; 3036-Q; 3036-R; 3036-S; 3036-T; 3036-U; 3036-V; 3052; 3054; 3057; 3071; 3073; 3074; 3075; 3078; 3081; 3082; 3087; 3088; 3090; 3108; 3109; 3109-A; 3111; 3112; 3112-A; 3114; 3117; 3118; 3119; 3119A; 3120; 3121; 3122; 3122-A; 3123; 3124; 3130; 3131; 3132; 3133; 3139; 3140; 3141; 3142; 3143; 3143-A; 3145; 3147; 3148; 3151; 3152; 3154; 3168; 3169; 3170; 3171; 3171-A; 3174; 3175; 3175-A; 3178; 3180; 3181; 3182; 3183; 3184; 3184-A; 3189; 3191; 3192; 3193; 3193-A; 3196; 3198; 3199; 3200; 3201; 3202; 3203; 3204; 3205; 3206; 3215; 3216; 3217; 3218; 3220; 3222; 3226; 3227; 3231; 3232; 3232-A; 3234; 3235; 3235-A; 3237; 3238; 3239; 3240; 3241; 3242; 3242-A; 3248; 3249; 3250; 3251; 3251-A; 3253; 3254; 3255; 3256; 3257; 3258; 3259; 3260; 3265; 3266; 3267; 3268; 3269; 3273; 3287; 3288; 3289; 3289-A; 3291; 3292; 3293; 3293-A; 3296; 3297; 3298; 3299; 3300; 3301; 3302; 3303; 3303-A; 3316; 3317; 3318; 3319; 3319-A; 3332; 3333; 3334; 3335; 3337; 3338; 3339; 3340; 3341; 3342; 3343; 3344; 3345; 3346; 3347; 3349; 3350; 3351; 3372; 3373; 3373-B; 3374; 3375; 3376; 3377; 3379.

The corticosteroid field, i.e., the compounds and their use as pharmacologically active agents is well documented, and numerous other references exist which describe the synthesis and use of corticosteroids as depicted above by StOH. Substantially any corticosteroid having a hydroxyl group at the C-21 position of the molecule is useful as the parent steroid in forming the novel esters of the present invention. The compounds of Formulas A and B represent preferred corticosteroids used to contribute the St moiety of the compounds of Formula I. Particularly preferred corticosteroids which are useful in forming the esters of Formula I are the following: hydrocortisone, cortisone, corticosterone, prednisone, prednisolone, 6α-methylprednisolone, triamcinolone, dexamethasone, betamethasone, flumethasone, 11-deoxy corticosterone, fluprednisoline, 9α-fluorohydrocortisone, flurandrenolone, paramethasone, chlorprednisone, and dehydrocorticosterone. The compounds of Formula I wherein n is 4 to 9, and particularly 4 to 6, are more preferred. Also the compounds of Formula I wherein Y is a bond and X is

are more preferred.

Lower alkyl of from 1 to 4 carbon atoms includes methyl, ethyl, n-propyl, n-butyl, and isopropyl, and when optionally substituted by one hydroxyl illustrative of such groups are 2-hydroxyethyl, 2-hydroxypropyl and 3-hydroxypropyl.

Illustrative examples of pharmaceutically acceptable base addition salts of the compounds of Formula I are alkali metal salts or organic tertiary amine salts as formed by treatment with a suitable base as set forth hereinbelow.

The compounds of Formula I are prodrugs of the corticosteroids represented by the St moiety in said Formula and have the same utility as the known or parent corticosteroid. Thus the compounds of Formula I are useful in treating warm blooded animals, e.g., dogs, cats, monkeys, horses, and particularly humans for various disease conditions. For example, the compounds of Formula I are useful in those situations where one wishes to elicit an anti-inflammatory, anti-pruritic or vasoconstrictive action inherent in the parent corticosteroid. The compounds of the present invention and the compounds utilized in the novel formulations of the present invention are particularly useful in treating acute adrenal insufficiency (Addison's disease); allergic conditions such as asthma, contact dermatitis, serum sickness, angioneurotic edema, drug hypersensitivity reactions and anaphylactoid reactions; collagen and musculoskeletal diseases, such as, rheumatoid arthritis, dermatomyositis, lupus erythematosus, rheumatic fever; dermatological diseases, such as, pemphigus and severe erythema multiforme; ulcerative colitis, and acute exacerbations of multiple sclerosis. Also when the parent corticosteroid contributing the St moiety of the compounds of Formula I possesses mineralocorticoid properties said compounds of Formula I are useful particularly in maintaining a physiological electrolyte level in patients with acute adrenal insufficiency.

Although the compounds of Formula I and salts thereof may be administered orally, these compounds are designed for and have their primary application in those situations where oral therapy is not feasible. The compounds of Formula I are best suited for administration as sterile aqueous solutions by intravenous injection, intravenous infusion, or intramuscular or subcutaneous injection, or intravenous bolus.

The novel compounds of the present invention provide marked advantages over known corticosteroids or derivatives thereof in that these novel compounds are highly water soluble and when formulated in a manner which fully exploits the advantageous physicochemical properties of these compounds are sufficiently stable in aqueous solution to afford long term storage of solutions of said novel compounds.

The solution stability of these compounds is due to several features: (1) The derivatives are highly soluble in the pH range 4 to 5 which is the pH range in which ester hydrolysis in aqueous solution is minimized. (2) The sulfonate group is sufficiently distant from the ester linkage that any catalytic effect or undesirable substituent effect on the ester hydrolysis is minimal. (3) The compounds self-associated in concentrated solutions to form molecular aggregates which increase the shelf life of formulations by (a) retarding hydroxide ion catalyzed ester hydrolysis at high concentrations, and (b) solubilizing any parent corticosteroid present in and resulting from the hydrolysis of a solution of a compound of the present invention.

The solution stability of the compounds of Formula I varies to some extent depending on the nature of X and Y and the values for m and n. Shown in Table I are estimates of $t_{90\%}$ (time for 10% hydrolysis) of various derivatives in dilute aqueous solutions at 25° C. These estimates are based on an extrapolation of the rate constants for acid and base catalyzed hydrolysis to the pH at which hydrolysis is a minimum. The rate constants for acid and base catalyzed hydrolysis were determined at pH 2 and 8, respectively, in 0.01 ionic strength buffers.

TABLE I

| Example | Estimated $t_{90\%}$ (years) |
|---------|------------------------------|
| 1 | 3.9 |
| 2 | 3.9 |
| 3 | 4.1 |

The actual shelf-life of formulations of the above compounds would be expected to differ from the above estimates for two reasons: (1) The solubility of the parent corticosteroid formed on hydrolysis may be exceeded prior to 10% degradation of the ester. Micelle formation by the intact prodrugs of Formula I results in solubilization of free corticosteroid thereby prolonging shelf-life. For example, the solubility of methylprednisolone in a 0.11 molar aqueous solution of the compound of Example 2 is approximately twenty times that in water. The degree of solubilization varies with the ester concentration, nature of the pro-moiety, and the structure of the corticosteroid. (2) Micelle formation by the intact prodrug in concentrated solutions results in stabilization of the ester linkage toward base catalyzed hydrolysis. For example, the base catalyzed hydrolysis rate in a 0.11M solution of the compound of Example 1 is less than one-half the rate in a $5 \times 10^{-4}$M solution.

In addition to the effects of formulation concentration, pH and storage temperature have a dramatic impact on the stability of formulations. However, in formulations buffered at a pH at or near the pH-hydrolysis rate minimum (4–5) and stored at room temperature (25° C.), the compounds of the present invention are solution stable for several months, regardless of concentration. The stability or shelf-life of solutions of compounds of the present invention can be prolonged by decreasing the storage temperature, e.g., to temperatures from 4° C. to 24° C.

As indicated previously, the compounds of Formula I exhibit stability in water only when the pH of their solution is properly controlled. Ideally, the pH will be maintained at a level where the hydrolysis of the ester is at a minimum. This minimum depends to a certain degree on the chemical structure of the pro-moiety, the formulation concentration, and the temperature of storage but in general will be at a pH of about 4 to 5 for the compounds of this invention. Most advantageously, buffers should be employed to maintain the pH at or near the desired level throughout the shelf life of the formulation. Suitable buffers are those which are physiologically acceptable and exhibit sufficient buffer capacity in the pH range 4–5, e.g., acetate, citrate, succinate, or phthalate buffers and the like. The quantity of buffer used is determined by means known in the art and will depend on the pH desired, the concentration of the solution, and the buffering capacity of the buffer.

The concentration of the solution stable formulations of the compounds of Formula I depends on the activity level of and the ultimate dose of parent corticosteroid desired. In general the stability of the formulations increases as the concentration of novel ester increases. In essence the solution stable formulations may be as concentrated as viscosity properties permit or until the solubility of the novel ester is exceeded. Inasmuch as the compounds of the present invention are converted to the parent corticosteroid in vivo, ideally the concentration of the novel ester and the volume of the solution administered will be chosen to provide a quantity of parent corticosteroid which is known to be effective. For example, a 0.267M solution of the compound in Example 3, set forth below, is equivalent to 100 mg/ml of 6α-methylprednisolone.

Sterile aqueous solutions of the compounds of Formula I typically will contain other components such as preservatives, anti-oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Typical formulations useful in practicing the present invention are set forth below.

Since the compounds of Formula I are prodrugs of the parent corticosteroids, their efficacy depends on bioconversion to liberate the free corticoid in vivo. Bioconversion of these commpounds was demonstrated in two species: rats and monkeys.

One female Sprague-Dawley rat was surgically prepared by implanting cannulae into the femoral vein and femoral artery. The animal was administered an amount of the compound of Example 3 equivalent to 30 mg/kg methylprednisolone intravenously and 200 μl blood samples were withdrawn from the arterial catheter, at one minute, 2 minutes, 5 minutes, 15 minutes, 45 minutes, and 2 hours, quenched immediately in 2–4 ml of 18% MeOH/H$_2$O containing 1.25% HOAc and stored over dry ice. The samples were analyzed for methylprednisolone by HPLC. The blood level of methylprednisolone peaked in 2 minutes at a concentration of 17

μg/ml indicating rapid bioconversion to the free corticoid.

The bioconversion of the compound of Example 1 was demonstrated in four female Rhesus monkeys which were administered the compound intravenously at a dose of 1.5 mg/kg (methylprednisolone equivalents). Blood samples were withdrawn at 5 minutes, 15 minutes, 30 minutes, one, 2 and 4 hours and analyzed for free methylprednisolone by HPLC. Peak blood levels of methylprednisolone were observed between 5 and 15 minutes after dosing suggesting rapid bioconversion of the compound of Example 1 to free methylprednisolone.

The compounds of Formula I may be prepared by various means, and it will be apparent from the following that the ester moiety attached at the 21-position of the steroid, St, may be introduced by reaction of the steroid with an appropriate starting material sulfonate which provides the entire moiety, or said ester moiety may be introduced by a sequence of one or more reactions.

In preparing the compounds of Formula I wherein Y is oxy, i.e., —O—, equimolar amounts of an intermediate of the formula

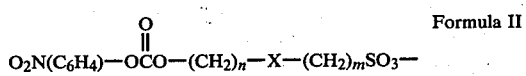  Formula II wherein (C$_6$H$_4$) is 1,4-phenylene and n, m, and X have the meanings defined in Formula I, and a parent steroid of the formula StOH wherein St has the meaning defined in Formula I are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°-60° C. with stirring until all the activated carbonate ester is consumed. The product is purified by pouring the reaction mixture into water with the pH adjusted to ~4 and washing with an organic solvent, e.g., ether or ethyl acetate. It is then concentrated by removing the solvent and further purified either as the free acid or as an appropriate salt by crystallization and/or chromatography.

The compounds of Formula I wherein Y is a bond are prepared by reacting equimolar amounts of an intermediate of the formula

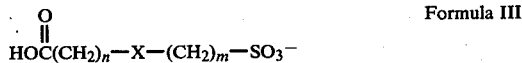  Formula III wherein n, m, and X have the meanings defined in Formula I with a 21-iodo or 21-O-mesyl derivative of the parent steroid which may be represented respectively by the formulas St-Iodo   Formula IV and St-O-mesyl   Formula V wherein St has the meaning defined in Formula I and mesyl means —S(O$_2$)—CH$_3$. When the 21-iodo steroid derivative is employed the reaction proceeds at room temperature, whereas when the 21-O-mesyl steroid derivative is used the reaction is heated to about 60°-70° C. The reaction is carried out in a dry aprotic solvent such as DMF in the presence of a sterically hindered tertiary amine such as diisopropylethylamine. The product is isolated by diluting with water, adjusting the pH to ~5, washing with an organic solvent, suitably ethyl acetate, and further purifying by recrystallization or chromatography.

Compounds of Formula I wherein Y is a bond and X is

may also be prepared by reacting equimolar amounts of a 21-iodo steroid derivative of Formula IV and a bis-acid of the formula

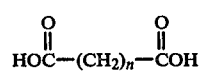  Formula VI wherein n has the meaning defined in Formula I in a dry aprotic solvent such as THF or DMF in the presence of a sterically hindered amine such as diisopropylethylamine with optional heating to give an intermediate of the formula

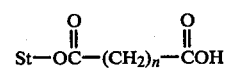  Formula VII which is activated by cooling to about −20° to −10° C. and reacting with isobutyl chloroformate in the presence of a tertiary amine, such as triethylamine for about 10-20 minutes during which time the reaction mixture is permitted to warm. To the activated derivative of Formula VII is added an appropriate aminoalkylsulfonate of the formula

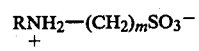  Formula VIII wherein m and R have the meanings defined in Formula I. This latter reaction is complete within an hour, and the product is isolated by standard procedures, e.g., washing an aqueous solution, pH 5, with an appropriate organic solvent such as ethyl acetate, and purification by crystallization and/or chromatography.

Alternatively in preparing the compounds of Formula I wherein Y is a bond and X is

, to the above obtained activated derivative of Formula VII is added p-nitrophenol in the presence of a tertiary amine such as triethylamine to give a stable intermediate of the formula

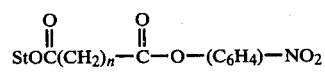  Formula IX wherein St and n have the meanings defined in Formula I and (C$_6$H$_4$) is 1,4-phenylene. The intermediate of Formula IX is then reacted with a molar equivalent of an aminoalkylsulfonate of Formula VIII in a dipolar aprotic solvent such as THF or DMF in the presence of a base such as pyridine. The Formula I product is then isolated by washing an aqueous solution at pH 5 with an organic solvent, such as ethyl acetate, and purifying by crystallization and/or chromatography.

To form base addition salts of the compounds of Formula I said compounds are treated with suitable pharmaceutically acceptable inorganic or organic bases by standard procedures. Suitable inorganic bases are, for example, those of alkali metal hydroxides such as potassium and sodium. Suitable organic bases are physiologically acceptable compounds containing tertiary amine functional groups, for example, trialkylamines such as triethylamine.

The compounds of Formula II wherein X is

are prepared by heating to about 60° C. a suitable aliphatic lactone, such as, propiolactone, γ-butyrolactone, δ-valerolactone, ε-caprolactone, etc., as n in Formula I increases in length, with an equimolar amount of an ω-aminoalkylsulfonate of Formula VIII in an aprotic solvent such as DMSO, DMF or THF to give the acyclic amide which is isolated by standard extractive procedures. The amide is reacted with p-nitrophenylchloroformate in a dry aprotic solvent such as THF in the presence of pyridine and isolated by standard procedures to give the compounds of Formula II or used without isolation to form compounds of Formula I.

The compounds of Formula II wherein X is

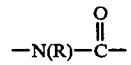

are prepared by reacting an appropriate ω-sulfo alkanoic acid having an alkylene chain length of from 1 to 5 carbon atoms with an ω-amino alcohol of the formula HO—$(CH_2)_n$—NHR, wherein n and R have the meanings defined in Formula I, in a dry aprotic solvent, such as THF or DMF, in the presence of dicyclohexylcarbodiimide (DCC) to yield the amide. Any ester formed by reaction at the wrong end of the amino alcohol is eliminated by selective hydrolysis. Alternatively, a cyclic anhydride of Formula D (see Formula Chart) such as 3-sulfopropionic anhydride is reacted with an ω-amino alcohol in a polar aprotic solvent in the presence of a tertiary amine to form the amide. The product is isolated by standard extractive methods, and the product is taken up in a dry aprotic solvent and treated with p-nitrophenylchloroformate in the presence of pyridine to give the compounds of Formula II which may be isolated by standard procedures.

The compounds of Formula II wherein X is oxy are prepared by reacting a suitable α,ω-aliphatic diol of the formula HO$(CH_2)_n$—OH wherein n has the meaning defined in Formula I with an ω-halosulfonate of formula Z—$(CH_2)_m SO_3$— where Z=Cl, Br, I, —Omesyl, or —Otosyl and m is as defined in Formula I, or, alternatively, with a sultone of Formula C (see Formula Chart) wherein m is as defined in Formula I, in a dry aprotic solvent in the presence of one equivalent of potassium t-butoxide to yield the desired ether. This compound is purified by standard extractive methods, then is reacted with p-nitrophenyl chloroformate in a dry aprotic solvent in the presence of pyridine to give a reactive mixed p-nitrophenyl carbonate ester of Formula II.

To prepare the compounds of Formula II wherein X is sulfur, an aliphatic ω-halo alcohol of the formula HO$(CH_2)_n$—halo wherein n is as defined in Formula I and halo is chloro, bromo, or iodo is reacted with thiourea in refluxing lower alcohol to yield an isothiouronium salt which is then cleaved by treating the compound with an aqueous base to yield an ω-mercaptoalkanol HS$(CH_2)_n$OH—. The ω-mercapto alkanol, after isolation via standard methods, e.g., distillation, is then reacted with an ω-bromoalkylsulfonic acid of formula Br$(CH_2)_m SO_3 H$ wherein m is as defined in Formula i or a sultone of Formula C in a solution containing two equivalents of inorganic base in water. A water miscible solvent (e.g., alcohol) may also be added to solubilize the reactants. The product of formula HO$(CH_2)_n S(CH_2)_m SO_3$— is isolated by standard extractive procedures. Final purification is achieved by recrystallization and/or chromatography. This product may be oxidized at this stage to give a sulfoxide or sulfone if desired, or it may be maintained in the sulfide form. To form the sulfoxide, i.e., X is —S(O)—, the sulfide is treated with one equivalent of sodium metaperiodate in aqueous lower alcohol at 0° C. When oxidation is complete the sodium iodate is filtered out and the sulfoxide isolated by standard procedures. To form the sulfone, i.e., X is —S($O_2$)—, the sulfide is reacted with 30% $H_2O_2$ in 50% acetic acid at room temperature for several hours. Oxidation proceeds through the sulfoxide to the sulfone. The product is isolated by standard procedures, with final purification being achieved by recrystallization or by chromatography if needed. The sulfur-linked hydroxyl containing sulfonate is then converted to a reactive mixed carbonate ester by combining it with an equimolar quantity of p-nitrophenylchloroformate in an aprotic solvent with added pyridine to give the compounds of Formula II which may be isolated by standard procedures.

The compounds of Formula III wherein X is

are prepared by reacting an aminoacid of the formula HN(R)$(CH_2)_n$—COOH with a bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in aqueous alcohol and treated with sodium bisulfite to give the compounds of Formula III which are isolated by standard procedures. Alternatively, the ω-amino acid may be reacted with a cyclic anhydride of Formula D (see Formula Chart) wherein m has the meaning defined in Formula I in an aprotic solvent or in aqueous media in the presence of a tertiary amine to yield the compounds of Formula III.

The compounds of Formula III wherein X is

are prepared by reacting an appropriate alkylene dicarboxylic acid with an appropriate aminoalkylsulfonate by procedures well known in the art.

The compounds of Formula III wherein X is oxy are prepared using t-butyl ester of a carboxylic acid of the formula

wherein n is as defined in Formula I and halo is Cl, Br or I. This ester is prepared by reacting an appropriate ω-halo alkanoic acid of formula HOOC(CH$_2$)$_n$—halo with isobutylene gas in a dry aprotic solvent in the presence of catalytic amounts of sulfuric acid. The t-butyl ester is reacted with an ω-hydroxyalkyl sulfonic acid of formula HO(CH$_2$)$_m$SO$_3$H wherein m is as defined in Formula I in a dry aprotic solvent in the presence of a strong base such as potassium t-butoxide to yield an ether. The ether is isolated by standard methods well known in the art and the carboxylic acid is deprotected by treatment with trifluoroacetic acid. The compound of Formula III is isolated by removing trifluoroacetic acid and solvent under reduced pressure.

The compounds of Formula III wherein X is sulfur are prepared by reaction of an ω-mercaptocarboxylic acid of the formula HOOC(CH$_2$)$_n$SH and an ω-bromoalkyl sulfonic acid of formula Br(CH$_2$)$_m$SO$_3$H or a sultone of Formula C wherein n and m are as defined in Formula I in water containing three equivalents of inorganic base. A water miscible organic solvent, such as THF, may be added if required to solubilize the reactants. After several hours at 30°-50° C. the reaction is complete and the sulfide is isolated by extractive methods to give the compounds of Formula III.

The compounds of Formula III wherein X is sulfoxide are obtained by treating the corresponding Formula III compound wherein X is sulfur with sodium periodate in water at 0° to 10° C. for ~10-20 hours. The aqueous solution is diluted with at least two volumes of acetonitrile, NaIO$_3$ precipitate is filtered out, and the product is isolated by standard methods. The compounds of Formula III wherein X is sulfone are obtained by treating the corresponding sulfur compound with 30% hydrogen peroxide in 50% acetic acid for several hours at room temperature. The product is again isolated by standard procedures.

The compounds of Formulas IV and V are prepared by general procedures well known in the art. The bisacids of Formula VI and the aminoalkylsulfonates of Formula VIII are known in the art or are prepared by means well known in the art. Also, the other starting materials described hereinabove including the ω-aminoalcohols, the α,ω-aliphatic diols, the ω-halosulfonates, the compounds of Formula C, the ω-haloalcohols, the ω-amino acids, the compounds of Formula D, and the ω-hydroxyalkylsulfonic acids are commercially available, or are known in the art or prepared by procedures generally known in the art.

The following examples further illustrate the invention.

EXAMPLE 1

N-Methyl taurine amide of methylprednisolone 21-hemisuccinate (Na salt)

A THF solution (15 ml) containing 2.37 g (5 mmol) methylprednisolone 21-hemisuccinate and 0.8 ml (5.7 mmol) triethylamine in a 3-neck flask flushed with N$_2$ and immersed in a dry ice-acetone bath was treated with 1.75 ml (5.7 mmol) of isobutylchloroformate. The flask was allowed to warm to room temperature resulting within 15 minutes in the formation of a white precipitate (triethylamine HCl). To the reaction mixture was then added a solution (85 ml THF; 20 ml H$_2$O; 15 ml t-butylalcohol) containing 0.8 g (5 mmol) N-methyl taurine (Na salt) and 0.8 ml triethylamine. Product formation, monitored by HPLC, was complete in 20 minutes.

The crude reaction mixture was diluted with water (150 ml), adjusted to pH 4.5-5, and washed with ethyl acetate (2×150 ml). The aqueous phase at pH 4 was then extracted with butanol (4×50 ml). The butanol layers were combined and solvent was removed under reduced pressure. The compound was further purified by passing a 70% THF-water solution through a strong cation exchange column (Na$^+$ form). Solvent was removed under reduced pressure and the residue was redissolved in methanol and precipitated on addition of acetonitrile.

Analysis: NMR(Unisol®-d): Δ=7.4 (d, 1, C$_1$—H), 6.2 (d, 1, C$_2$—H), 5.9 (s, 1, C$_4$—H), 5.0 (q, 2, C$_{21}$—H$_2$), 4.4 (broad, 1, C$_{11}$—H), 2.6-3.1 (m, 21-sidechain).

UV: λmax=243 nm; Σ=14,100.

HPLC: (254 uv detector) >99% apparent purity.

EXAMPLE 2

(a) Methylprednisolone 21-hemisuberate

To a solution of 17.6 g octanedioic acid (0.1 mole) and 17.5 ml diisopropylethylamine (0.1 mole) in 100 ml DMF was added a DMF solution (50 ml) containing 10 g of methylprednisolone 21-iodide (0.02 mole). The reaction mixture was allowed to stand at room temperature overnight after which the reaction mixture was concentrated under reduced pressure (50° C.) and dissolved in ethyl acetate (500 ml). Repeated extractions with water (500 ml) adjusting the biphasic mixture to pH 6.0 (dilute NaOH) were carried out until the final pH of the aqueous phase remained constant. This procedure removed excess amine and dicarboxylic acid. The organic layer was evaporated in vacuo leaving an off-white solid residue which was dissolved in hot acetone-methanol and recrystallized after addition of hexane, m.p. 188°-191° C.

(b) Taurine amide of methylprednisolone 21-suberate (Na salt)

A dry THF solution (25 ml) containing 1.12 g (2.1 mmol) of the product of Example 2(a) and 0.35 ml (2.5 mmol) triethylamine in a 3-neck flask flushed with N$_2$ and cooled to 10° C. was treated with 0.33 ml isobutyl chloroformate and stirred 15 minutes at ~10° C. The resulting suspension was added dropwise to a solution (35 ml H$_2$O; 35 ml THF) containing 1 g taurine (8 mmol) maintaining the pH at ~8 by addition of triethylamine.

The reaction mixture was diluted with H$_2$O (100 ml) and washed with ethyl acetate (150 ml). The pH was then adjusted to 0.7 with HCl and extracted with butanol. The solvent was removed under reduced pressure. Further purification was obtained by reversed-phase preparative chromatography of the free acid. Extraction of the product into butanol and titration with sodium bicarbonate to an apparent equivalence point at pH 4.3 was followed by solvent removal, dissolution in methanol and precipitation upon the addition of isopropanol.

Analysis: UV: λmax=243 nm; Σ=14,700.

HPLC: (254 nm uv detector) single peak—no free methylprednisolone present.

EXAMPLE 3

N-Methyltaurine amide of methylprednisolone 21-hemisuberate (Na salt)

A dry THF solution (10 ml) containing 0.65 g (1.2 mmol) of the product of Example 2(a) and 0.2 ml (1.4 mmol) of triethylamine flushed with $N_2$ and cooled to about $-10°$ C. with dry ice/acetone was treated with 0.18 ml (1.4 mmol) of isobutylchloroformate. After stirring ~15 minutes a solution (10 ml THF:5 ml $H_2O$) containing 0.2 g N-methyltaurine (Na salt) was added. The pH of the solution was maintained at 7-7.5 during the reaction. Amide formation was very rapid and nearly quantitative (by HPLC).

The reaction mixture was diluted with water (~100 ml) and after pH adjustment to ~5 was washed with ethyl acetate (2×100 ml). The aqueous phase was then acidified with HCl and extracted with butyronitrile repeatedly. Addition of water and pH adjustment to ~5 with dilute NaOH resulted in the extraction of product into water. The aqueous phase at pH 5 was extracted repeatedly with butanol and the combined organic layers were evaporated under reduced pressure. The remaining residue was redissolved in methanol and ethyl acetate was added slowly resulting in precipitation of product.

Analysis: UV: λmax=243 nm; Σ=14,400.

HPLC: (254 nm uv detector) >98% apparent purity—no free methylprednisolone detected.

EXAMPLE 4

Hydrocortisone, 21-[6-[[3-sulfopropyl]amino]-6-oxohexyl carbonate]

5.5 ml of Σ-caprolactone is heated with 8 g of 3-amino-1-propane-sulfonic acid, sodium salt in dry DMF to form the desired amide. The product is isolated by removing solvent under reduced pressure and treated with 10 g of p-nitrophenylchloroformate in 100 ml THF containing 4 ml pyridine. When the chloroformate is consumed the solution is reacted with 15 g hydrocortisone, 3.4 ml of pyridine, and 1 g of dimethylaminopyridine. The resulting solution is heated until the desired reaction is complete. The reaction mixture is diluted with water, adjusted to pH ~5, and washed with ethyl acetate. The aqueous phase is then adjusted with HCl to pH 1-2 in the presence of butanol and extracted repeatedly with butanol to isolate the free acid in the organic solvent. Final purification is accomplished by chromatography and/or crystallization.

EXAMPLE 5

Dexamethasone, 21-[6-[[4-sulfo-1-oxobutyl]amino]hexanoate]

To a DMF solution (100 ml) containing 6.5 g 6-aminocaproic acid and 8.7 ml diisopropylethylamine is added 6.8 g 1,4-butane sultone. The reaction mixture is heated at 45° C. for several hours to yield the desired amide intermediate.

To the above product is added an additional 8.7 ml diisopropylethylamine and 25 g of the 21-iodo derivative of dexamethasone prepared by methods well known in the art in 100 ml DMF. The mixture is heated to ~65° C. and the reaction progress is monitored by HPLC. Upon completion of the reaction, water (500 ml) is added, the pH is adjusted to 5, and the solution is washed with ethyl acetate (500 ml). The aqueous solution is then acidified to pH 1-2 with HCl and extracted repeatedly with butanol to isolate the free acid in the organic solvent. Final purification is accomplished by chromatography and/or crystallization.

EXAMPLE 6

Methylprednisolone, 21-[6-[2-sulfoethoxy]hexanoate]

Isobutylene gas is bubbled into a THF (100 ml) solution containing 9.75 g 6-bromocaproic acid and a catalytic amount of sulfuric acid resulting in the formation of the t-butylester of 6-bromocaproic acid. When the acid is completely esterified, excess isobutylene is removed under reduced pressure and 6.4 g of hydroxyethane sulfonic acid (Na salt) and 5.6 g of potassium tert-butoxide are added. Upon completion of ether formation the product is isolated by diluting the reaction mixture with water (200 ml), adjusting pH to 5, and washing with ethyl acetate. The aqueous layer is then adjusted to pH 1-2 and the product is extracted into butanol. Removal of solvent under reduced pressure results in isolation of the protected ether product. Deprotection is carried out by treatment with trifluoroacetic acid at room temperature. After removal of solvents under reduced pressure the ether is reacted with 20 g of 21-iodomethylprednisolone in 100 ml DMF in the presence of 17.4 ml of diisopropylethylamine. Ester formation is monitored by HPLC. When the reaction is complete, the solvents are removed under reduced pressure and the residue is redissolved in 500 ml $H_2O$. The pH of the solution is adjusted to ~5 and washed with 500 ml ethyl acetate. The aqueous layer is then acidified (HCl) to a pH of 1-2 and extracted repeatedly with butanol. The butanol layers containing the desired product are combined and solvent is removed under reduced pressure. Further purification of the free acid or an appropriate salt is achieved by chromatography and/or crystallization.

EXAMPLE 7

Methylprednisolone, 21-[3-[[4-sulfobutyl]thio]propionate]

To 100 ml of a THF-water solution containing 5.3 g of 3-mercaptopropionic acid and 6.8 g of 1,4-butane sultone is added slowly (with stirring) 50% NaOH solution to maintain a pH of 11-12. After several hours at 30°-50° C. the consumption of base is complete, and the pH is adjusted to ~3 with dilute sulfuric acid. The sulfide intermediate is isolated by removal of solvent and recrystallization. A 5.8 g quantity of the sulfide (monosodium salt) is then dissolved in DMF (100 ml) and reacted with 10 g of 21-iodo methylprednisolone in the presence of 4.4 ml diisopropylethylamine to give the corresponding ester. Excess solvent is removed from the reaction mixture under reduced pressure and the residue is redissolved in 300 ml $H_2O$. The pH of the solution is adjusted to ~5 and the solution is washed with 300 ml ethyl acetate. The aqueous layer is then acidified to pH 1-2 and extracted repeatedly with butanol. The solvent is removed from the combined butanol layers and the desired product is further purified by crystallization and/or chromatography.

EXAMPLE 8

Methylprednisolone, 21-[3-[[4-sulfobutyl]sulfinyl]propionate]

In 100 ml of water cooled to 0° C., 11.6 g of the sulfide intermediate (monosodium salt) prepared as described in Example 7 is treated with 4.4 g of sodium metaperiodate. When the reaction is complete, sodium iodate is removed by filtration, the pH is adjusted to ~3, and solvent is removed under reduced pressure. The sulfoxide intermediate is further purified by crystallization and a 6.2 g quantity of the product is then dissolved in 100 ml DMF and reacted with 10 g methylprednisolone 21-iodide in the presence of 4.4 ml diisopropylethylamine. The desired product is isolated as described in Example 7.

EXAMPLE 9

Methylprednisolone, 21-[3-[[4-sulfobutyl]sulfonyl]propionate]

The title compound is prepared in a manner corresponding to that in Example 8 except that the sulfide intermediate prepared in Example 7 is oxidized to the corresponding sulfone by dissolving 4.6 g of the sulfide in 40 ml of 50% aqueous acetic acid and 5 ml of 30% hydrogen peroxide. When the reaction to form sulfone is complete the intermediate is isolated as described in Examples 7 and 8 and used in the synthesis of the desired ester as described in Example 7.

EXAMPLE 10

When in the procedure of Example 2(a) an appropriate amount of the 21-iodide of triamcinolone, dexamethasone, betamethasone, flurandrenolone, prednisone, fluprednisolone, hydrocortisone, cortisone, corticosterone, dehydrocorticosterone, prednisolone, flumethasone, 11-deoxycorticosterone, 9α-fluorohydrocortisone, chlorprednisolone or paramethasone is substituted for methylprednisolone 21-iodide the following intermediates are obtained:

triamcinolone 21-hemisuberate,
dexamethasone 21-hemisuberate,
betamethasone 21-hemisuberate,
flurandrenolone 21-hemisuberate,
prednisone 21-hemisuberate,
fluprednisolone 21-hemisuberate,
hydrocortisone 21-hemisuberate,
cortisone 21-hemisuberate,
corticosterone 21-hemisuberate,
dehydrocorticosterone 21-hemisuberate,
prednisolone 21-hemisuberate,
flumethasone 21-hemisuberate,
11-deoxycorticosterone 21-hemisuberate,
9α-fluorohydrocortisone 21-hemisuberate,
chlorprednisolone 21-hemisuberate,
paramethasone 21-hemisuberate.

When in the procedure of Example 2(b) an appropriate amount of each of the above obtained intermediates is substituted for methylprednisolone hemisuberate the following respective products are obtained:

Taurine amide of triamcinolone 21-hemisuberate.HCl,
Taurine amide of dexamethasone 21-hemisuberate.HCl,
Taurine amide of betamethasone 21-hemisuberate.HCl,
Taurine amide of flurandrenolone 21-hemisuberate.HCl,
Taurine amide of prednisone 21-hemisuberate.HCl,
Taurine amide of fluprednisolone 21-hemisuberate.HCl,
Taurine amide of hydrocortisone 21-hemisuberate.HCl,
Taurine amide of cortisone 21-hemisuberate.HCl,
Taurine amide of corticosterone 21-hemisuberate.HCl,
Taurine amide of dehydrocorticosterone 21-hemisuberate.HCl,
Taurine amide of prednisolone 21-hemisuberate.HCl,
Taurine amide of flumethasone 21-hemisuberate.HCl,
Taurine amide of 11-deoxycorticosterone 21-hemisuberate.HCl,
Taurine amide of 9α-fluorohydrocortisone 21-hemisuberate.HCl,
Taurine amide of chlorprednisolone 21-hemisuberate.HCl,
Taurine amide of paramethasone 21-hemisuberate.HCl.

EXAMPLE 11

When in the procedure of Example 4 an appropriate amount of triamcinolone, dexamethasone, methylprednisolone, betamethasone, flurandrenolone, prednisone, fluprednisolone, cortisone or paramethasone is substituted for hydrocortisone the following respective products are obtained.

triamcinolone, 21-[6-[[3-sulfopropyl]amino]-6-oxohexylcarbonate],
dexamethasone, 21-[6-[[3-sulfopropyl]amino]-6-oxohexylcarbonate],
betamethasone, 21-[6-[[3-sulfopropyl]amino]-6-oxohexylcarbonate],
flurandrenolone, 21-[6-[[3-sulfopropyl]amino]-6-oxohexylcarbonate],
prednisone, 21-[6-[[3-sulfopropyl]amino]-6-oxohexylcarbonate],
fluprednisolone, 21-[6-[[3-sulfopropyl]amino]-6-oxohexylcarbonate],
methylprednisolone, 21-[6-[[3-sulfopropyl]amino]-6-oxohexylcarbonate],
cortisone, 21-[6-[[3-sulfopropyl]amino]-6-oxohexylcarbonate],
paramethasone, 21-[6-[[3-sulfopropyl]amino]-6-oxohexylcarbonate].

EXAMPLE 12

When in the procedure of Example 9 an appropriate amount of the 21-iodo derivative of hydrocortisone, methylprednisolone, triamcinolone, betamethasone, flurandrenolone, prednisone, fluprednisolone, cortisone or paramethasone is substituted for the 21-iodo derivative of dexamethasone the following respective products are obtained:

triamcinolone, 21-[6-[[4-sulfo-1-oxobutyl]amino]hexanoate,
betamethasone, 21-[6-[[4-sulfo-1-oxobutyl]amino]hexanoate,
flurandrenolone, 21-[6-[[4-sulfo-1-oxobutyl]amino]hexanoate,
prednisone, 21-[6-[[2-aminoethyl]amino]-6-oxo-hexyl
fluprednisolone, 21-[6-[[4-sulfo-1-oxobutyl]amino]hexanoate,
cortisone, 21-[6-[[4-sulfo-1-oxobutyl]amino]hexanoate,
paramethasone, 21-[6-[[4-sulfo-1-oxobutyl]amino]hexanoate,
hydrocortisone, 21-[6-[[4-sulfo-1-oxobutyl]amino]hexanoate,
methylprednisolone, 21-[6-[[4-sulfo-1-oxobutyl]amino]-hexanoate.

The following examples are illustrative of typical formulations of representative compounds of the present invention.

EXAMPLE 13

N-Methyltaurine amide of hydrocortisone 21-succinate (Na salt): 163.0 mg
(Equivalent to 100 mg hydrocortisone)
Dilute NaOH to adjust pH to 4.5
Sterile water for injection to make 1 ml

EXAMPLE 14

N-Methyltaurine amide of methylprednisolone 21-suberate (Na salt): 180.0 mg
(Equivalent to 100 mg methylprednisolone)
Acetic acid: 2.0 mg
Sodium acetate: 2.0 mg
Benzyl alcohol: 8.8 mg
HCl (dilute) or NaOH (dilute) to adjust pH to 4.75
Sterile water for injection to make 1 ml

EXAMPLE 15

Dexamethasone 21-[6-[[4-sulfo-1-oxobutyl amino]hexanoate] (equivalent to 20 mg dexamethasone): 33.4 mg
Creatinine: 8.0 mg
Acetic acid: 4.0 mg
Sodium acetate: 4.0 mg
Sodium bisulfite: 1.0 mg
Disodium edetate: 0.5 mg
Metylparaben: 1.5 mg
Propylparaben: 0.2 mg
HCl (dilute) or NaOH (dilute) to adjust pH to 4.75
Water for injection to make 1 ml

FORMULA CHART

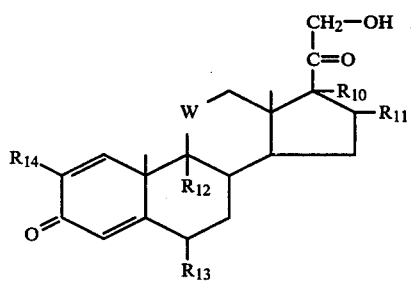

Formula A

In the above Formula A:

ω is

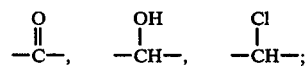

$R_{10}$ is H, α-OH;
$R_{11}$ is H, α-CH$_3$, β-CH$_3$, α-F, β-F, α-OH or =CH$_2$;
$R_{12}$ is H, F, Cl, Br;
$R_{13}$ is H, α-F, α-CH$_3$, β-CH$_3$, α-Cl, β-Cl, β-OH;
$R_{14}$ is H, CH$_3$.

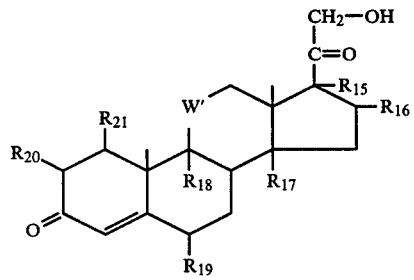

Formula B

-continued
FORMULA CHART

In the above Formula B:

W' is

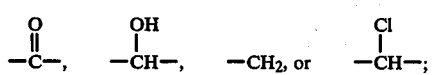

$R_{15}$ is H, α-OH, α-CH$_3$;
$R_{16}$ is H, α-OH, α-CH$_3$;
$R_{17}$ is H, α-OH;
$R_{18}$ is H, α-F, β-F, α-Br, α-Cl, α-OH;
$R_{19}$ is H, β-OH, α-CH$_3$, β-CH$_3$, α-F, α-Cl;
$R_{20}$ is H, α-F, Cl, α-CH$_3$, =CH$_2$;
$R_{21}$ is H, α-OH; with the proviso that one of $R_{20}$ and $R_{21}$ is hydrogen; preferably $R_{17}$, $R_{20}$ and $R_{21}$ are hydrogen.

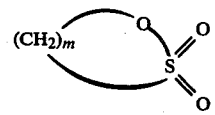

Formula C

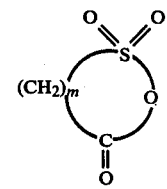

Formula D

We claim:
1. A compound of the formula

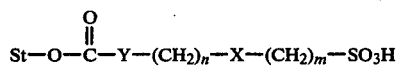

wherein
St is a corticosteroid absent the C-21 hyroxyl of said corticosteroid;
Y is a bond or —O—;
X is

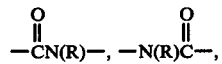

—O—, —S—, —S(O)—, or —S(O$_2$)—;
n is an integer of from 2 to 9;
m is an integer of from 1 to 5; with the proviso that the sum of m and
n is not greater than 10;
R is H or lower alkyl of from 1 to 4 carbon atoms; and salts thereof with the proviso that when n is 2, R is other than hydrogen.

2. A compound of claim 1 wherein n is 4 to 9.
3. A compound of claim 2 wherein Y is a bond.
4. A compound of claim 2 wherein X is

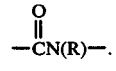

5. A compound of claim 3 or 4 wherein n is 4 to 6.
6. A compound of claim 4 wherein n is 4 to 6.
7. A compound of claim 2 wherein the corticosteroid forming the St moiety is 6α-methylprednisolone, hydrocortisone, corticosterone, prednisone, prednisolone, triamcinolone, dexamethasone, betamethasone, flumethasone, 11-deoxycorticosterone, fluprednisolone, 9α-fluorohydrocortisone, paramethasone, chlorprednisone or dehydrocorticosterone.

8. A compound of claim 7, which is the N-methyltaurine amide of methylprednisolone 21-hemisuberate, sodium salt.

9. A compound of claim 7 which is the taurine amide of methylprednisolone 21-suberate, sodium salt.

10. A compound of claim 7 which is 21-[6-[[3-sulfopropyl]amino]-6-oxohexylcarbonate]hydrocortisone.

11. A compound of claim 1 which is the N-methyltaurine amide of methylprednisolone 21-succinate, sodium salt.

12. A pharmaceutical composition comprising an effective quantity of a compound of claim 1 as a sterile aqueous solution.

13. A composition of claim 9 which is in unit dosage form.

14. A composition of claim 12 wherein the compound is the

N-methyltaurine amide of methylprednisolone 21-hemisuccinate, sodium salt, taurine amide of methylprednisolone 21-suberate, sodium salt, 21-[6-[[3-sulfopropyl]amino]-6-oxohexylcarbonate]hydrocortisone, N-methyl-taurine amide of methylprednisolone 21-hemisuberate, sodium salt.

* * * * *